(12) United States Patent
Lipkowitz et al.

(10) Patent No.: US 11,367,146 B2
(45) Date of Patent: Jun. 21, 2022

(54) LIFE INSURANCE POLICY APPLICATION PROCESS AND SYSTEM

(71) Applicant: Yeroosha, Inc., Miami, FL (US)

(72) Inventors: Elizabeth Leah Lipkowitz, Westmount (CA); David Emmanuel Kakon, Westmount (CA); Israel Kohn, Westmount (CA)

(73) Assignee: Yeroosha, Inc., Miami, FL (US)

( * ) Notice: Subject to any disclaimer, the term of this patent is extended or adjusted under 35 U.S.C. 154(b) by 0 days.

(21) Appl. No.: 17/373,848

(22) Filed: Jul. 13, 2021

(65) Prior Publication Data

US 2022/0051343 A1 Feb. 17, 2022

Related U.S. Application Data

(63) Continuation-in-part of application No. 16/991,838, filed on Aug. 12, 2020, now abandoned.

(51) Int. Cl.
*G06Q 40/08* (2012.01)
*G06Q 10/10* (2012.01)
*G06Q 30/00* (2012.01)
*G06Q 50/18* (2012.01)
*H04L 12/18* (2006.01)
(Continued)

(52) U.S. Cl.
CPC .......... *G06Q 40/08* (2013.01); *G06F 21/602* (2013.01); *G06Q 10/105* (2013.01); *G06Q 20/085* (2013.01); *G06Q 30/018* (2013.01); *G06Q 50/18* (2013.01); *G16H 10/20* (2018.01); *H04L 12/18* (2013.01); *H04L 67/12* (2013.01)

(58) Field of Classification Search
CPC ........ G06Q 40/00; G06Q 40/02; G06Q 40/08; G06Q 50/22; G06Q 50/24
See application file for complete search history.

(56) References Cited

U.S. PATENT DOCUMENTS 8,543,425 B1 * 9/2013 Hacker .................. G06Q 40/08
705/4
2002/0111835 A1 * 8/2002 Hele ...................... G06Q 40/08
705/4

(Continued)

OTHER PUBLICATIONS

Mastroeni ("Pricing of insurance policies against cloud storage price rises", Jun. 15, 2012, pp. 1-4).*

*Primary Examiner* — Gregory A Pollock
(74) *Attorney, Agent, or Firm* — Mark Terry

(57) ABSTRACT

A method, system, and non-transitory computer-readable medium for facilitating insurance policy application processing over a communications network includes a processor configured for accepting input data from a customer, accepting further data from the insurance agent, creating a first data structure, encoding changes to the first data structure based on the input data and the further data, and populating the first data structure, generating ancillary documents and transmitting to the customer, creating a second data structure encoding changes to the second data structure based on the first data structure, and populating the second data structure, and transmitting, the second data structure to a third party to initiate transmission of a health questionnaire to the customer. The system further includes a first memory for storing the first data structure and a second memory for storing the second data structure.

20 Claims, 5 Drawing Sheets

(51) Int. Cl.
*G16H 10/20* (2018.01)
*G06F 21/60* (2013.01)
*H04L 67/12* (2022.01)
*G06Q 20/08* (2012.01)

(56) References Cited

U.S. PATENT DOCUMENTS

| | | | |
|---|---|---|---|
| 2002/0124177 A1* | 9/2002 | Harper | G06F 21/6245 |
| | | | 713/189 |
| 2012/0016692 A1 | 1/2012 | Jenkins-Robbins | |
| 2013/0191168 A1 | 7/2013 | Klimek | |
| 2017/0026519 A1* | 1/2017 | Charlson | H04M 3/42008 |

* cited by examiner

LIFE INSURANCE POLICY APPLICATION PROCESS AND SYSTEM

CROSS-REFERENCE TO RELATED APPLICATIONS

This application is a continuation-in-part of patent application number 16991838 filed on Aug. 12, 2020, and entitled "Life Insurance Policy Application Process and System." The subject matter of patent application number 16991838 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The claimed subject matter relates to business processes executed via a computing device, and more specifically, the claim subject matter relates to a process for facilitating the application process for insurance coverage.

BACKGROUND

While around for more than 200 years, the life insurance industry has grown in recent years. In fact, in 2018 alone, the life insurance industry was responsible for almost 1 trillion dollars in revenue in the United States. While this number may seem large, in 2019 only 57% of adults in the United States actively held life insurance policies (a number that was down from the previous year and has continued to drop), and most of those life insurance policies are for policy amounts less than needed. In large part, the low and declining percentage of Americans purchasing life insurance is due to the difficulties connecting life insurance agents and brokers with consumers, or procuring leads, as well as the complicated application process that eventually turns a lead into a sale. As a result of these wide-felt issues, consumers and professionals engaging with or operating in the life-insurance space face many uphill battles in the sale and procurement of life insurances policies. In many cases, consumers are burdened out of the gate with an overwhelming number of options to consider, ranging not only from which individual agent, broker, or company to choose, but also which term and amount to choose. If the consumer is able to discern which options are best for them, they are then subject to a daunting application process that takes them through various representatives, nurses, and other medical professionals, and that requires due diligence and affirmative actions on the consumer's part—an overall lengthy and undesirable process. Agents and others operating as professionals in the space experience the opposite side of the same burdens. The burdens of obtaining leads and thereafter maintaining leads throughout the application process while making the process as smooth and easy for the potential customer are perhaps the largest and most widely felt burdens in the industry. In short, most Americans are not applying for insurance policies because the process of applying is lengthy and cumbersome.

Obtaining leads and turning them into sales has consistently been one of the more difficult aspects of a life insurance agent or broker's day-to-day operations. Presently, leads are generated in a variety of ways that require agents, brokers, and their companies substantial time and money with little to no guarantee of future profits. In some scenarios, these costs to individual agents are offset when they become part of a company that provides leads to them. However, even in situations where the individual agent has not lost time or money, the company has certainly expended money acquiring said leads and the agent continues to expend time converting the lead into a sale. Apart from obtaining leads from an employer, the most common ways of obtaining leads today can be broken down into three main categories—purchased leads, leads resulting from marketing and advertising, and direct contact leads. Each of these categories can cost considerable amounts of time and money to those looking to secure new leads, and often ignore or fail to engage consumers who are actively and readily looking for life insurance. These methods of obtaining leads also come with their own shortfalls apart from the amount of time and money spent with no guaranteed sale. The purchase of leads, for example, does not always guarantee an agent or broker exclusive access to the list they have purchased, requiring them to invest even more time in money and maintaining a competitive edge over other agents and brokers who may have purchased the same list. In addition to these shortfalls, agents and brokers must navigate through this portion of the process in manner that keeps the potential customer engaged and interested, a task that is difficult considered the complex nature of the application process. Further, any existing methods that expedite the process of obtaining a life insurance policy has an added cost to the customer to account for adverse selection.

As mentioned above, the post-lead application process is hardly secondary to obtaining a lead in its burdensome nature. In most cases, potential customers must find an agent or broker before this portion even begins. Once started, the customer is often bombarded with calls and emails, requests for documentation, request for medical examination, and often required to meet a slew of other requirements that may vary from company to company. While customers come in hoping for a quick and easy process, the medical examination stage alone can delay the process by up to two weeks or more. For the agent, maintaining communication and seeing the sale through is equally as difficult and the scattered nature of the process, requiring consumers to cause the potential customer to act on the requests above, and do so honestly, in order to see the process through to policy issuance and final payment.

As a result of the substantial shortcomings in the process for receiving leads, filing applications, and making the resulting sales, the need exists for a centralized and streamlined method of doing so. Specifically, the need exists for a centralized method and system for communicating leads to licensed agents and facilitating the life insurance application process that begins out of said leads.

SUMMARY

A method, system, and non-transitory computer-readable medium for facilitating insurance policy application processing over a communications network is disclosed. The system comprises processor configured for providing a user interface configured for accepting input data from a customer, accepting further data from the insurance agent, creating a first data structure composed of strings, attributes of strings, dependencies between strings, and hierarchies between strings, encoding changes to the first data structure based on the input data and the further data, and populating the first data structure based on the input data and the further data, generating one or more ancillary documents based on the first data structure and transmitting to the customer, over the communications network, the one or more ancillary documents for electronic signature by the customer, creating a second data structure composed of strings, attributes of strings, dependencies between strings, and hierarchies between strings, encoding changes to the second data structure based on the first data structure, and populating the second data structure by mapping data from the first data structure, and transmitting, via the communications network, the second data structure to a third party to initiate transmission of a health questionnaire to the customer. The system further includes a first memory for storing the first data structure and a second memory for storing the second data structure.

Additional aspects of the claimed subject matter will be set forth in part in the description which follows, and in part will be obvious from the description, or may be learned by practice of the claimed subject matter. The aspects of the claimed subject matter will be realized and attained by means of the elements and combinations particularly pointed out in the appended claims. It is to be understood that both the foregoing general description and the following detailed description are exemplary and explanatory only and are not restrictive of the disclosed subject matter, as claimed.

BRIEF DESCRIPTION OF THE DRAWINGS

The accompanying drawings, which are incorporated in and constitute part of this specification, illustrate embodiments of the claimed subject matter and together with the description, serve to explain the principles of the claimed subject matter. The embodiments illustrated herein are presently preferred, it being understood, however, that the claimed subject matter is not limited to the precise arrangements and instrumentalities shown, wherein:

DETAILED DESCRIPTION OF THE DRAWINGS

The disclosed embodiments improve upon the issues identified within the prior art by facilitating the process for completing applications for life insurance. Specifically, the disclosed embodiments improve over the prior art by centralizing and streamlining the life insurance application process from the initial stage of customer engagement to final policy issuance using an automated process executed over a communications network such as the Internet or the public switched telephone network (PSTN). This prevents customers and agents from having to be in one another's physical presence to complete the process, and additionally allows agents to complete the process from anywhere they may find themselves with a wireless internet or cellular connection.

The disclosed embodiments further improve over the prior art by streamlining the process, as mentioned above. This is done by reducing the complexity of the application process through the use of conditional logic that operates to allow agents to ask the fewest questions while continuing to cover the broad scope of life insurance applications. This improvement is further evidenced by the inclusion of automated processes such as interactive voice response (IVR), data scraping, e-sign services, etc.

The disclosed embodiments further improve upon the prior art by significantly reducing the time spent on the application process and maintaining direct and exclusive communication between the life insurance agent and their potential customer. Using the automated process listed above in conjunction with an accelerated underwriting process, customers can expect significantly shorter wait times for receiving their policy than presently is permitted by the conventional life insurance application process.

The disclosed embodiments further improve over the prior art by improving the functioning of the claimed computer itself. In particular, as discussed above, the claimed process with the first and second data structures allows the computer to use to less memory than required for conventional document formats, results in faster computation time (i.e., generating the first and second data structures, encoding changes to the structures and populating them) without expending large amounts of processing time, disk storage and user experience, as occurs with conventional document formats. These are also improvements in the technology of insurance application form processing. The claimed embodiments are an innovation in computer technology, namely insurance application form processing, which in this case reflects both an improvement in the functioning of the computer and an improvement in another technology.

Figure 1:
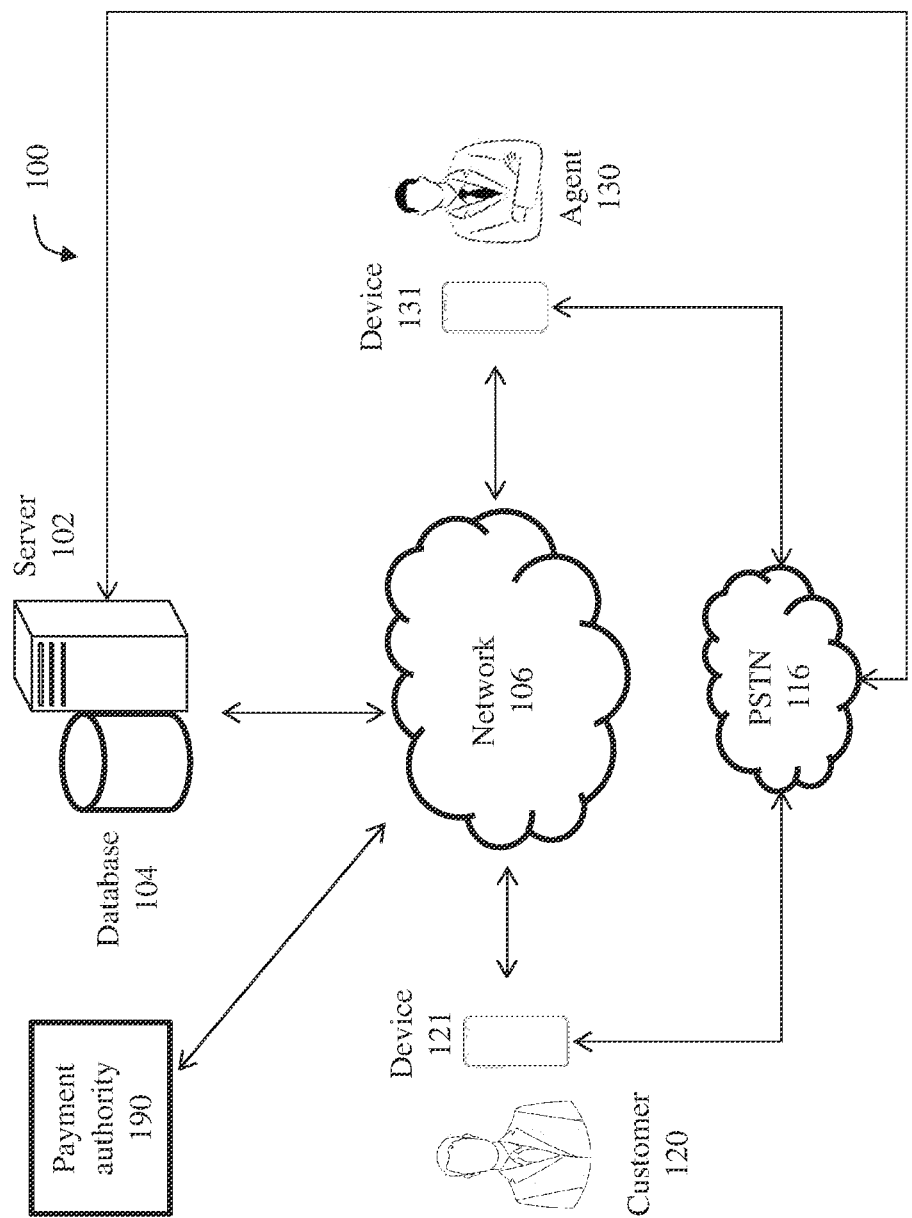
FIG. 1 is a block diagram illustrating the network architecture of a system for facilitating the life insurance policy application process, in accordance with one embodiment.

Referring now to the drawing figures in which like reference designators refer to like elements, there is shown in FIG. 1 an illustration of a block diagram showing the network architecture of a system 100 for facilitating the life insurance policy application process. A prominent element of FIG. 1 is the server 102 associated with repository or database 104 and further communicatively coupled with network 106, which can be a circuit switched network, such as the Public Service Telephone Network (PSTN), or a packet switched network, such as the Internet or the World Wide Web, the global telephone network, a cellular network, a mobile communications network, or any combination of the above. Server 102 is a central controller or operator for functionality of the disclosed embodiments, namely, facilitating the life insurance application process.

FIG. 1 includes mobile computing devices 121 and 131, which may be smart phones, mobile phones, tablet computers, handheld computers, laptops, or the like. In addition, FIG. 1 includes customer 120 and agent 130, which are the corresponding users to mobile devices 121 and 131, respectively. Customer 121 is a consumer seeking an insurance policy such as life insurance, homeowner's insurance, business insurance or the like. Agent 130 is a licensed insurance agent in the state where customer 120 is seeking to be insured. Agent 130 may be a licensed insurance agent with a company or an individual licensed insurance broker. FIG. 1 also shows a server 102 and database or repository 106, which may be a relational database comprising a Structure Query Language (SQL) database stored in a SQL server. The repository 104 serves data from a database during the course of operation of the disclosed embodiments. Database 104 may be distributed over one or more nodes or locations that are connected via network 106.

The database 104 may include a user or customer record for each customer 120 and an agent record for each agent 130. A user or customer record may include contact/identifying information for a person (username, first name, middle name, last name, address, telephone number, email address, etc.), healthcare and biological information for the person (pre-existing conditions, familial health history, present and past prescriptions, drug use, occupation, sex, gender expression, etc.), electronic payment information for the user, sales transaction data associated with the user, etc. A customer record may also include current location data about the user, a unique identifier for the user, a description of previous insurance policies held, or other relevant data for the customer. A customer record may further include demographic data for the user, such as age, income data, race, color, marital status, etc. An agent record may include similar information about the agent with the addition, this record may the agent's employer, insurance license, specializations, states of licensure, etc. A customer record may also include input data which may include data that is used by an insurance company to calculate an insurance premium quote or to determine whether the customer is eligible for coverage, such as the customer's age, the customer's gender, the customer's smoker status, the type of coverage desired, the amount of coverage desired, the length of the desired coverage (such as 10 years versus, 20 years for term life insurance) and the customer's personal information. A customer record may also include further data which may include additional data that is used by an insurance company to calculate an insurance premium quote or to determine whether the customer is eligible for coverage, such as customer activities, past history of the customer, etc. A customer record may also include data entered by the customer in a health-related form, such as health history, past history of certain disease, family history of certain diseases, name of regular doctor, etc.

Customer records and agent records may include sales transaction data, which may include one or more product/service identifiers (such as SKUs), one or more product/service amounts, buyer contact/identifying information, and electronic payment information. In one embodiment, electronic payment information may comprise buyer contact/identifying information and any data garnered from a purchase card (i.e., purchase card data), as well as any authentication information that accompanies the purchase card. Purchase card data may comprise any data garnered from a purchase card and any authentication information that accompanies the purchase card. In one embodiment, electronic payment information may comprise user login data, such as a login name and password, or authentication information, which is used to access an account that is used to make a payment.

Figure 5:
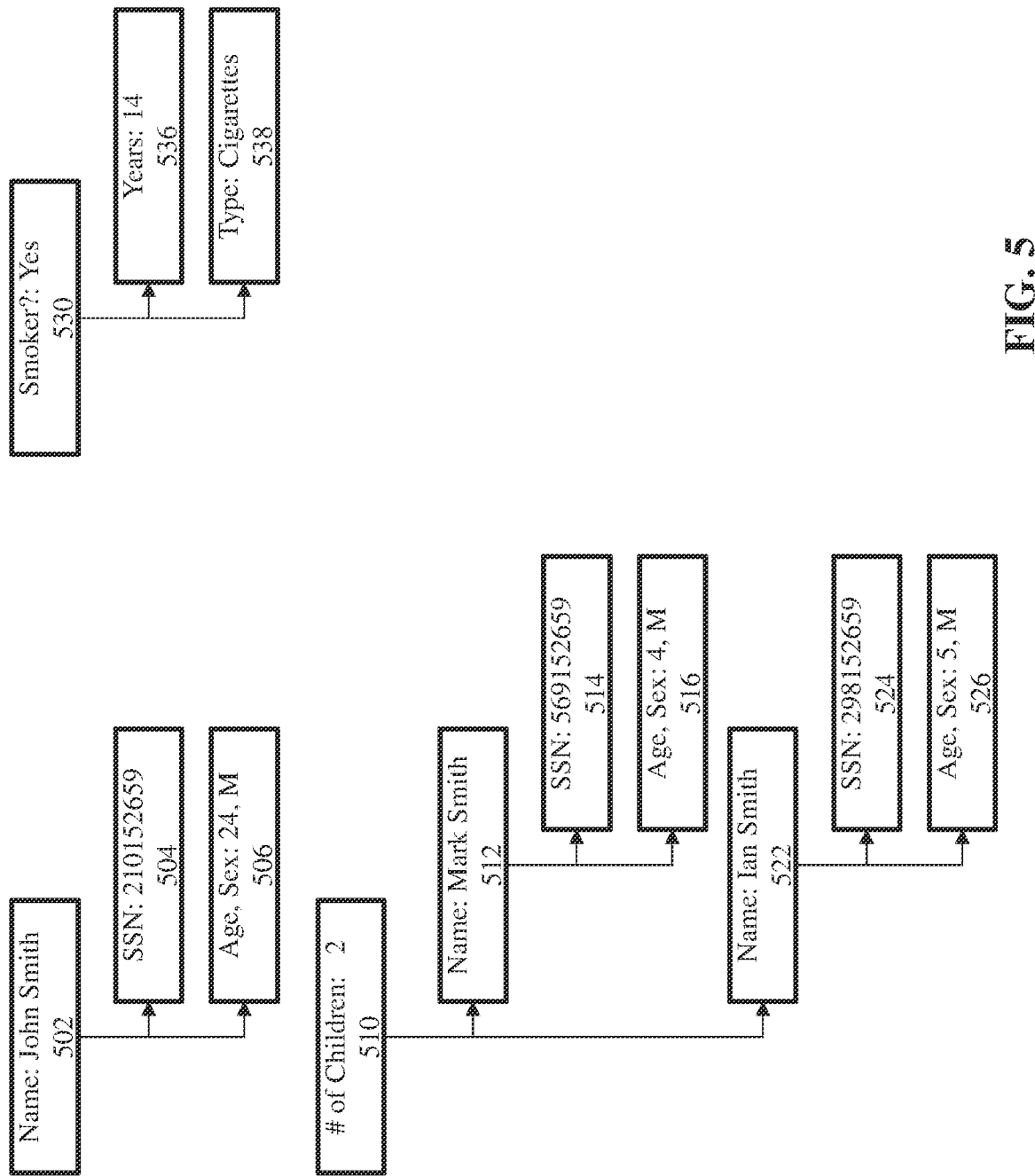
FIG. 5 is a block diagram of a data structure used in the claimed embodiments.

Database 104 may further store data structures especially configured for storing life insurance application data. The data structure is a life insurance application data organization, management, and storage format that enables efficient access and modification. More precisely, the data structure is a collection of life insurance application data values, the relationships among them, and the functions or operations that can be applied to the data, i.e., it is an algebraic structure about data. The algebraic structure consists of a set of values, a collection of operations that may be executed on the values, and a finite set of identities that the operations must satisfy. FIG. 5 provides a more detailed account of the data structure. Life insurance application data may include all of the data found in a customer or user record above.

FIG. 1 shows an embodiment wherein networked computing devices 121 and 131 interact with server 102 and database 104 over a network 106. It should be noted that although FIG. 1 shows only the networked computers 121, 131, and 102, the system of the disclosed embodiments supports any number of networked computing devices connected via network 106. Further, server 102, and units 121 and 131 may include program logic such as computer programs, mobile applications, executable files, or computer instructions (including computer source code, scripting language code or interpreted language code that may be compiled to produce an executable file or that may be interpreted at run-time) that perform various functions of the disclosed embodiments.

Note that although server 102 is shown as a single and independent entity, in one embodiment, the functions of server 102 may be integrated with another entity, such as one of the devices 121 or 131. Further, server 102 and its functionality, according to a preferred embodiment, can be realized in a centralized fashion in one computer system or in a distributed fashion wherein different elements are spread across several interconnected computer systems.

FIG. 1 also shows a payment authority 190, which acts to effectuate payments by customers 120. In the course of a sales transaction, server 102 may interface with payment authority 190 to effectuate payment. In one embodiment, the payment authority 190 is a payment gateway, which is an e-commerce Application Service Provider (ASP) service that authorizes and processes payments from one party to another. The payment authority 190 may accept payment via the use of purchase cards, i.e., credit cards, charge cards, bank cards, gift cards, account cards, etc.

FIG. 5 is a block diagram of a data structure (such as the data structure stored in the database 104 above) used in the claimed embodiments. Recall that a data structure is composed of strings, attributes of strings, dependencies between strings, and hierarchies between strings. A string is a sequence of characters, either as a literal constant or as a variable. The length of a string may be fixed or variable. A string may be considered as a data type and is often implemented as an array data structure of bytes (or words) that stores a sequence of elements, typically characters, using some character encoding. A hierarchy is an arrangement of items (in this case, strings) in which the items are represented as being superior to, subordinate to, or "at the same level as" one another. A hierarchy links items vertically to an item's immediate superior or to one of the item's subordinates. Each block in FIG. 5 shows an attribute-value pair, such as the pair "Name" and "John Smith" in block 502.

FIG. 5 shows an example wherein the string 502 with value "John Smith" has the attribute "Name" and therefore this string represents the name of the customer seeking life insurance. The string 504 has the attribute "social security number" and the string 506 holds the values of the age and sex of the customer. The vertical connection between the strings 504, 506 and string 502 indicate that strings 504, 506 are subordinate to, and must be associated with, a superior "Name" attribute string, such as string 502. This is part of the hierarchical structure of the data structure. The set of strings 502, 504, 506 hold the basic information for a "person."

Continuing, the string 510 holds the attribute "# of Children," which answers the question of how many children the customer has. Since the string 510 has the value 2 (i.e., the customer has two children), there are necessarily two sets of strings for two "persons." The first set of strings 512, 514, 516 hold the basic information for the first "person" named "Mark Smith" and the second set of strings 522, 524, 526 hold the basic information for the second "person" named "Ian Smith." The vertical connection between the strings 512, 522 and string 510 indicate that strings 512, 522 are subordinate to, and must be associated with, a superior "# of Children" attribute string, such as string 510. This is part of the hierarchical structure of the data structure. Note, however, that the number of "persons" under the string 510 is dependent on the value of string 510. Since string 510 has the value 2, there are necessarily two "persons" subordinate to string 510. In this way, the number of "persons" under string 510 is dependent on the value of the "# of Children" attribute string. This defines the dependencies that may be shown in the data structure.

FIG. 5 also shows the string 530 with value "Yes" and therefore this string represents that the customer is a smoker. The string 536 holds the value for the number of years the customer is a smoker and the string 538 holds the type of item smoked by the customer. The vertical connection between the strings 536, 538 and string 530 indicate that strings 536, 538 are subordinate to, and must be associated with, a superior "Smoker?" attribute string, such as string 530. This is part of the hierarchical structure of the data structure. But also, the existence of the strings 536, 538 in the data structure is dependent on the value of string 530. Since string 530 has the value "Yes", the strings 536, 538 necessarily exist. But if string 530 had the value "No", the strings 536, 538 would not exist. In this way, the existence of strings 536, 538 dependent on the value of the "Smoker?" attribute string. This defines the dependencies that may be shown in the data structure.

Figure 2:
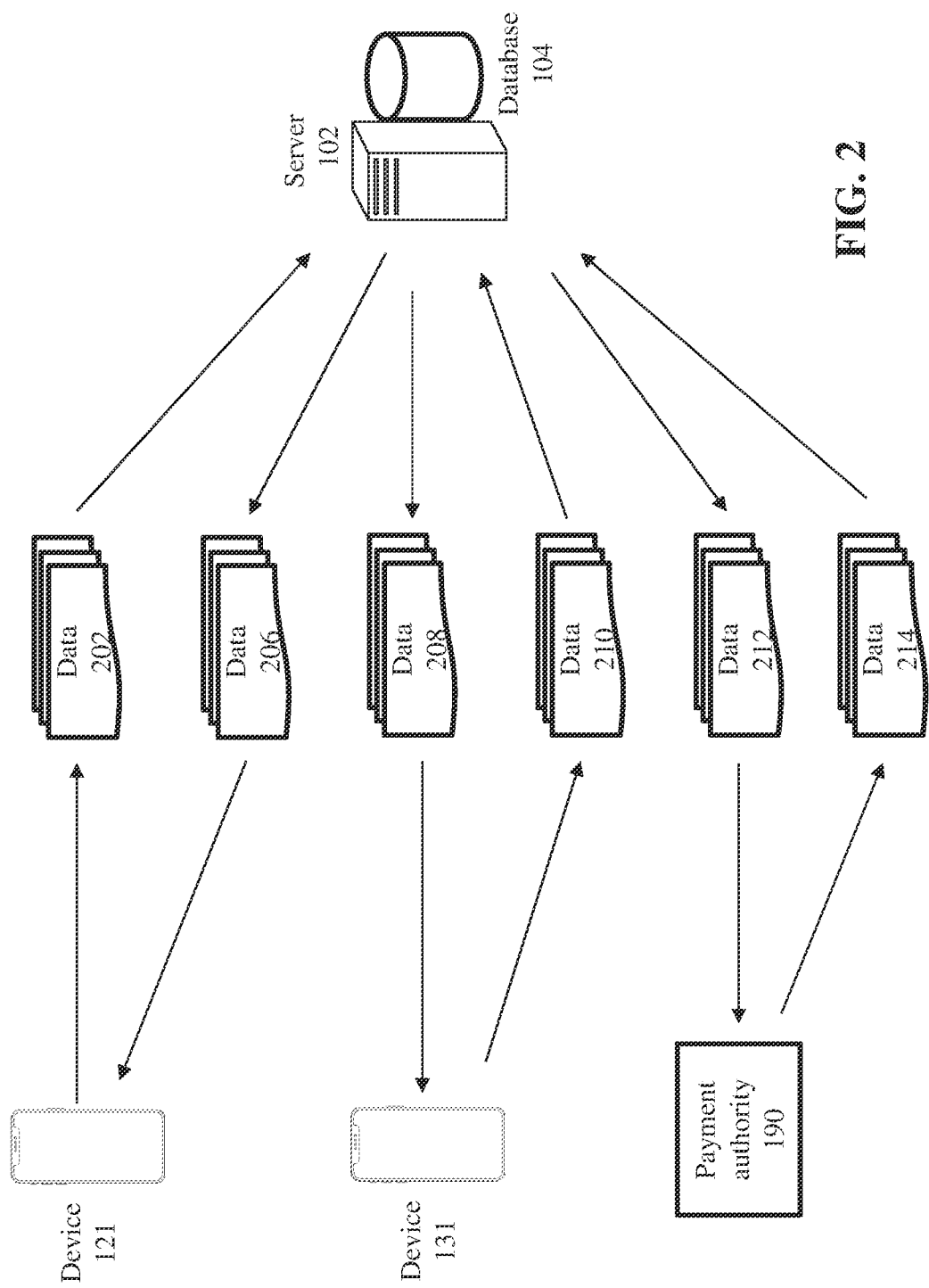
FIG. 2 is a block diagram showing the data flow of the process for facilitating the life insurance policy application process, according to one embodiment.
Figure 3:
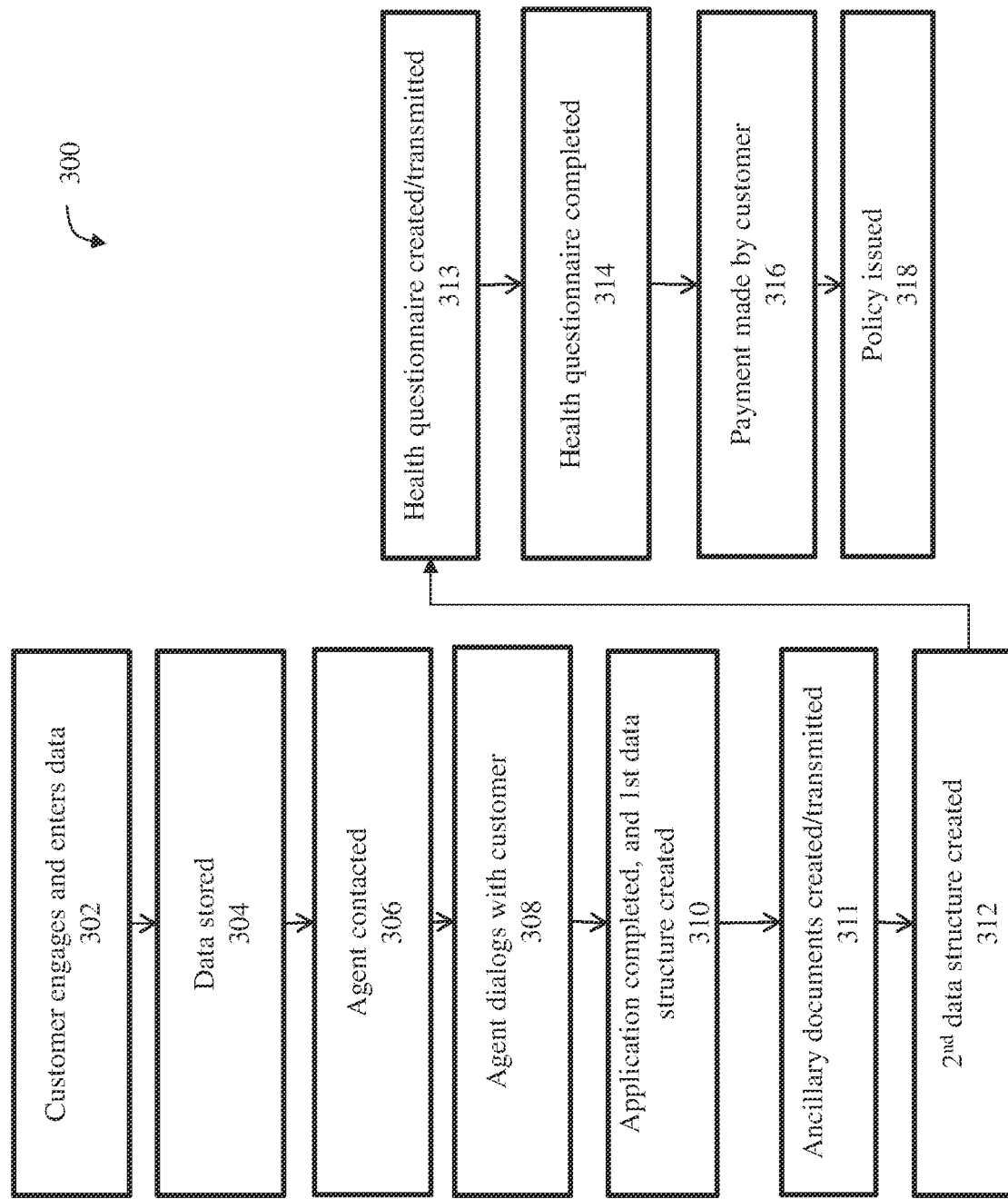
FIG. 3 is a flow chart depicting the general control flow of a process for facilitating the life insurance policy application process, according to one embodiment.

The process for facilitating the life insurance policy application process over a communications network will now be described with reference to FIGS. 2-3 below. FIGS. 2-3 respectively depict the data flow and control flow of the process for facilitating the insurance policy application process over a communications network 106, according to one embodiment. The process of the disclosed embodiments begins with step 302 (see flowchart 300, FIG. 3), wherein the customer 120 may initially engage or interact with server 102. Engagement may consist of an interaction by the customer 120 with a graphical user interface on a mobile application or a website, the initiation of a phone call, a response to a cold call, etc. In step 302, the user inputs into a mobile application, a web form, a website, via phone call, etc. input data (defined above) or any data that may be stored in a customer record. The server is configured for receiving said data upon completion (via data packet 202 over network 106). Data packet 202 may be made up of various types of data, including but not limited to voice, text, image, etc. In step 304, server 102 stores input data in a customer record in database 104.

The data input by the customer in step 302 (otherwise known as "input data") may include answers to questions posed in a web form. In one embodiment, said questions may include questions that are intended to filter out customers that may not qualify for the claimed process. For example, one said question may ask whether the customer has ever been denied life insurance for any reason. In said example, if the customer answers "Yes," then the customer is immediately notified that he does not qualify and is referred to another, separate, process. In another embodiment, step 302 comprises the customer entering the same data listed above (as being entered into a mobile application or web form) via IVR on a phone call.

During step 302, the server 102 processes any data input by the customer using a formula, so as to generate a premium quote for an insurance policy based on said processing. The formula may take into account any data that is used by an insurance company to calculate an insurance premium quote or to determine whether the customer is eligible for coverage, such as the customer's age, gender, smoker status, location, face value of policy, policy term length, the type of coverage desired, the amount of coverage desired, the customer's personal information, the customer activities, past history of the customer, and any data entered by the customer in a health-related form. The server 102 may communicate one or more premium quotes for an insurance policy to the customer using the method of engagement, such as web form, mobile application, IVR, etc.

The formula may comprise a reference table, lookup table or a multi-dimensional array that provides insurance premium quotes based on a variety of input values, such as age, gender, smoker status, location, face value and term length. Said lookup table or multi-dimensional array may provide an insurance premium quote for any permutation of the input values. Therefore, when a set of input values are defined, the reference table, lookup table or multi-dimensional array is queried to provide the premium quote.

In step 306, the server 102 broadcasts, over the communications network, a message (via data packet 208), to a group of available insurance agents (such as agent 130) licensed in the particular state where the customer 120 resides, the message indicating availability of the customer. The message may be sent via text, email, mobile application, etc. to the mobile computing devices of the agents, such as agent 130. In one embodiment, the message may prompt the group of available insurance agents to log into a secure system where the agent may view the new lead.

In one embodiment of step 306, the server 102 accesses a stored list or array of data in an attached database that defines (by phone number, email address or other unique identifier used to communicate with said agent) which insurance agents (such as agent 130) are licensed in the particular state where the customer 120 resides. Subsequently, once said subset of agents have been identified by the server, the server broadcasts, over the communications network, the message (via data packet 208), to said identified group of insurance agents (such as agent 130).

In one embodiment, a plurality of agents that are licensed in the state of the customer are notified at the same time, and each of said agents may view the message in a graphical user interface. Any of said agents may press on the message to indicate his acceptance or to indicate that he claims the lead. In one embodiment, an agent is required to input a PIN number to claim said lead.

Subsequently, one of said agents (such as agent 130) sends from his mobile device 131 (and server 102 receives) an acceptance (via data packet 210) from said agent 130 licensed in the particular state where the customer 120 resides. In one embodiment, the particular insurance agent may enter a 4-digit key into the secure system to claim the new lead. Lastly, in step 306, the server 102 transmits, over the communications network, a secure form (via data packet 208 or similar) to the particular insurance agent 130, wherein the form includes said input data and allows the agent to enter further data into the form.

In step 308, server 102 initiates a call, over the communications network 106 or PSTN 116, between the customer 120 and the particular insurance agent 130. In one embodiment, the call may be a VoIP call over network 106. Also in step 308, the server 102 transmits, over the communications network, a secure form (via data packet 208 or similar) to the particular insurance agent 130, wherein the form includes said input data and allows the agent to enter further data into the form. Further in step 308, the server 102 provides, over the communications network, an automated process that facilitates completion of the form. The automated process may include one or more of a bot, a web service or conditional logic that facilitates completion of the form by reducing an amount of data that must be input by the agent 130 into the form. Using conditional logic, the agent is guided to ask only the questions necessary until all fields are completed as required to complete the application for this use case Questions are presented to the agent in a sequence that is designed to facilitate the flow of information. During said call, the agent solicits further data from the customer, which the agent inputs into the secure web form.

The use of conditional logic (or conditional statements, conditional expressions, and conditional constructs) includes the use of a programming language that performs different computations or actions depending on whether a Boolean condition evaluates to true or false. As a result, the automated process that facilitates completion of the form eliminates questions that must be answered by the agent and/or customer and/or eliminates blanks that must be filled in by the agent and/or customer. For example, one question may ask whether the customer is married. The second question may ask how long the customer has been married. The automated process that facilitates completion of the form may detect that the answer to the first question is "no" or negative, and therefore eliminate the requirement that the second question be asked. In this way, the automated process that facilitates completion of the form eliminates questions that must be answered by the agent and/or customer and/or eliminates blanks that must be filled in by the agent and/or customer, thereby streamlining the process.

During the call, the agent may communicate one or more premium quotes for an insurance policy to the customer verbally on the call. The customer may choose which quote he selects, and the agent may enter this selection into the form.

Upon the reception of the further data entered by the agent, the form is completed by the agent 130, the call is terminated, and in step 310, the server 102 creates a first data structure, as described more fully in FIG. 5. The server 102 encodes changes to the first data structure based on the input data and the further data, and the server 102 populates the first data structure based on the input data and the further data. That is, the server 102 creates all of the attribute-value pairs of each block (such as blocks 502-538 in FIG. 5), creates the hierarchies between blocks (such as the superior-subordinate relationship between blocks 502 and 504), and all of the dependencies between the strings (such as the dependency between block 510 and blocks 512, 522). Then, the server populates the values for each attribute-value pair in the first data structure using the input data and the further data. The server 102 stores the first data structure in a first memory location. In one embodiment, the server 102 encrypts the first data structure before it is stored in the first memory location, so that any sensitive customer data may be secure from viewing by unauthorized parties. In step 310, part of the process may include entering agent data (from the agent record) into the form. Server 102 may also store any data input into the form into the relevant customer record in database 104.

In one embodiment, one or more of the elements of the data structure may be stored in an array. In another embodiment, dependencies where the number of dependent blocks may be variable, such as the dependency between block 510 and blocks 512, 522, are represented using linked lists. Note that although FIG. 5 shows only blocks 512, 522 depending from block 510, any number of blocks may depend from block 510, since the customer may have any number of children. In another embodiment, hierarchies where the number of subordinate blocks may be variable, such as the superior-subordinate relationship between block 502 and blocks 504, 506, are represented using linked lists. Note that although FIG. 5 shows only blocks 504, 506 subordinate to block 502, any number of blocks may be subordinate to block 502. In another embodiment, one or more of the elements of the data structure may be stored in an object data structure.

It should be noted that conventionally, the storage of life insurance application data is stored in conventional document formats, such as Portable Document Format (PDF). The problem with using such conventional document storage techniques is the large amount of data necessary to store life insurance application data, which often includes complex metadata such as hierarchies, dependencies, attributes, etc. The Portable Document Format required a large amount of storage space because this format includes data formatting for items such as vector graphics, raster images, interactive elements such as annotations, layers, rich media (including video content), and three-dimensional objects using U3D or PRC. The Portable Document Format also includes a header, objects, index table, and a footer. Consequently, the Portable Document Format requires a large amount of storage space to store what is sometimes a small amount of data. The advantage of the use of the first data structure is that it allows the computer to use to less memory than required for conventional document formats, such as PDF. This results in faster computation time (i.e., generating the first data structure, encoding changes to the structure, and populating it) without expending large amounts of processing time, disk storage and user experience, as occurs with conventional document formats.

In step 311, the server 102 generates a plurality of ancillary documents based on the input data and the further data that was entered, as encoded in the first data structure. The plurality of ancillary documents may further comprise an insurance carrier form and at least a legal agreement for the customer to sign with an electronic signature Also, the server 102 transmits to the customer (via data packet 206 or similar), over the communications network one or more of the plurality of ancillary documents for electronic signature by the customer. Also in step 311, the customer may sign (electronically) the at least one of the plurality of ancillary documents on his device 121. The server 102 receives said electronically signed at least one of the plurality of ancillary documents, such as via data packet 202 or similar.

In one embodiment, the process of transmitting to the customer (via data packet 206 or similar), over the communications network, one or more of the plurality of ancillary documents for electronic signature by the customer may include using a third-party electronic signature service, which receives from the server 102 the one or more of the plurality of ancillary documents and the third-party service contacts the customer directly for signature of the documents.

Subsequently, in step 312, the server 102 creates a second data structure, as described more fully in FIG. 5. The server 102 encodes changes to the second data structure based on the first data structure, and the server 102 populates the second data structure based on the first data structure. That is, the server 102 creates all of the attribute-value pairs of each block, creates the hierarchies between blocks, and all of the dependencies between the strings. Then, the server populates the values for each attribute-value pair in the second data structure by mapping the data in the first data structure to the second data structure. The server 102 stores the second data structure in a second memory location. In one embodiment, the server 102 encrypts the second data structure before it is stored in the second memory location, so that any sensitive customer data may be secure from viewing by unauthorized parties. If the first data structure was encrypted, then the processor unencrypts the first data structure before it is further used herein.

In one embodiment, the second data structure is created using a particular format that is distinct from the format of the first data structure. This is because the second data structure is used to prompt the creation and transmission to the customer of a health questionnaire which may have a different format than the format used for the first data structure. In said different format, the attribute-value pairs may be different, the dependencies may be different, and the hierarchies may be different. Therefore, a mapping function must be utilized. A mapping function is a mathematical algorithm that maps data from the format of the first data structure to the format of the second data structure. In this embodiment, the step of encoding changes to the second data structure based on the first data structure may include creating the hierarchies between blocks (in accordance with the second data structure format), and all of the dependencies between the strings (in accordance with the second data structure format). In this embodiment, the step of populating the values for each attribute-value pair in the second data structure includes utilizing the mapping function that maps data from the first data structure to the second data structure.

The mapping function may include conversion functions wherein source data from the first structure is read and converted into a different format for storage into the target data in the second data structure. For example, value data in the first data structure may be height data in feet and inches. In this example, the mapping function includes a conversion function wherein the height data is converted from feet/inches into meters, and the converted data is stored in the second data structure. In another example, the dependencies, such as the dependency between block 510 and blocks 512, 522, may be represented using linked lists in the first data structure but may be represented using arrays in the second data structure. Therefore, the mapping function maps data from the linked lists of the first data structure to the arrays of the second data structure. In another example, hierarchies, such as the superior-subordinate relationship between block 502 and blocks 504, 506, may be represented using linked lists in the first data structure but may be represented using arrays in the second data structure. Therefore, the mapping function maps data from the linked lists of the first data structure to the arrays of the second data structure. In another example, the dependencies, such as the dependency between block 510 and blocks 512, 522, may be represented as hierarchies in the second data structure. Therefore, the mapping function maps data from the dependencies of the first data structure to the hierarchies of the second data structure.

In step 313, server 102 creates a health questionnaire based on the data in the second data structure. Then, the server 102 transmits to the customer the health questionnaire for completion by the customer, to the customer's device 121 via data packet 206 or similar, wherein the health questionnaire includes questions about the customer's health. The server 102 may transmit the health questionnaire to other parties as well, such as the insurance carrier, and the agent.

The health questionnaire may be in particular format, and therefore, the second data structure may be in a format that is similar to, or configured to work with, the second data structure. The format of the second data structure may be distinct from the format of the first data structure. This is because the second data structure is used to prompt the creation and transmission to the customer of a health questionnaire which may have a different format than the format used for the first data structure. In said different format, the attribute-value pairs may be different, the dependencies may be different, and the hierarchies may be different. Therefore, a mapping function must be utilized to map data from the first to the second data structure.

In one embodiment of step 313, server 102 executes a module that automatically completes a web form (based on the data in the second data structure) and presses the relevant button on said web form that requests that a health questionnaire or form is sent to the customer. In one embodiment, this step comprises the server 102 generating a script in a scripting language, such as Selenium IDE, which script is then transmitted via network 106 to a remote server that executes that script. Said script is configured to automatically copy certain data from the second data structure, enters said data into said web form and presses the relevant button on said web form that requests that a health questionnaire or form is sent to the customer. In another embodiment, this step comprises the server 102 making an API call via network 106 to a remote server that executes that automatically reads certain data from the second data structure, enters said data into an API call and requests that a health questionnaire or form is sent to the customer.

Once the health questionnaire is completed by the customer in step 314, the customer submits the required payment (via data packet 212) to payment authority 190. In another embodiment, payment is made by the customer via check at the time of insurance policy delivery. Upon confirmation of payment, sent to server 102, via data packet 214, the customer may be issued their official life insurance policy as shown in step 318.

Note that steps 302-318 include limitations also recited in the claims such that the claims amount to significantly more than the mathematical operation recited in the step of creating the first data structure. There are several additional limitations recited in steps 302-318 and the claims besides the mathematical operation of creating the first data structure (creating a first data structure composed of strings, attributes of strings, dependencies between strings, and hierarchies between strings, encoding changes to the first data structure based on the input data and the further data, populating the first data structure based on the input data and the further data). The steps 302-318 and the claims also recite the steps of storing the first data structure in a first memory location and creating a second data structure and storing the second data structure in a second memory location. The steps 302-318 and the claims also recites the additional steps of generating ancillary documents based on the first data structure and transmitting those documents to the customer for electronic signature by the customer, as well as creating a second data structure, encoding changes to the second data structure based on the first data structure, populating the second data structure by mapping data from the first data structure. See also the data structure encrypting steps of claims 9, 15 and 20. These additional steps tie the mathematical operation (creating the first data structure) to the processor's ability to complete insurance application forms using previously entered data. These steps add meaningful limitations to the abstract idea of creating the first data structure and therefore add significantly more to the abstract idea than mere computer implementation. The steps 302-318 and the claims, when taken as a whole, do not simply describe the creation of a first data structure via a mathematical operation and storing data, but combines the steps of creating the first data structure with the steps for generating ancillary documents based on the first data structure and transmitting those documents to the customer for electronic signature by the customer, as well as creating a second data structure, encoding changes to the second data structure based on the first data structure, and populating the second data structure by mapping data from the first data structure. See also the data structure encrypting steps of claims 9, 15 and 20. By this, the claim goes beyond the mere concept of simply storing, retrieving, and combining data using a computer.

Finally, viewing the claim elements as an ordered combination, the steps recited in addition to the creation of the first data structure improve the functioning of the claimed computer itself. In particular, as discussed above, the claimed process with the first and second data structures allows the computer to use to less memory than required for conventional document formats, results in faster computation time (i.e., generating the first and second data structures, encoding changes to the structures and populating them) without expending large amounts of processing time, disk storage and user experience, as occurs with conventional document formats. These are also improvements in the technology of insurance application form processing. Unlike the invention in Alice Corp., the instant steps 302-318 and the claims are not merely limiting the abstract idea to a computer environment by simply performing the idea via a computer (i.e., not merely performing routine data receipt and storage or mathematical operations on a computer), but rather is an innovation in computer technology, namely insurance application form processing, which in this case reflects both an improvement in the functioning of the computer and an improvement in another technology. Taking all the additional claim elements individually, and in combination, the steps 302-318 and the claims as a whole amount to significantly more than the abstract idea of creating a first data structure.

Figure 4:
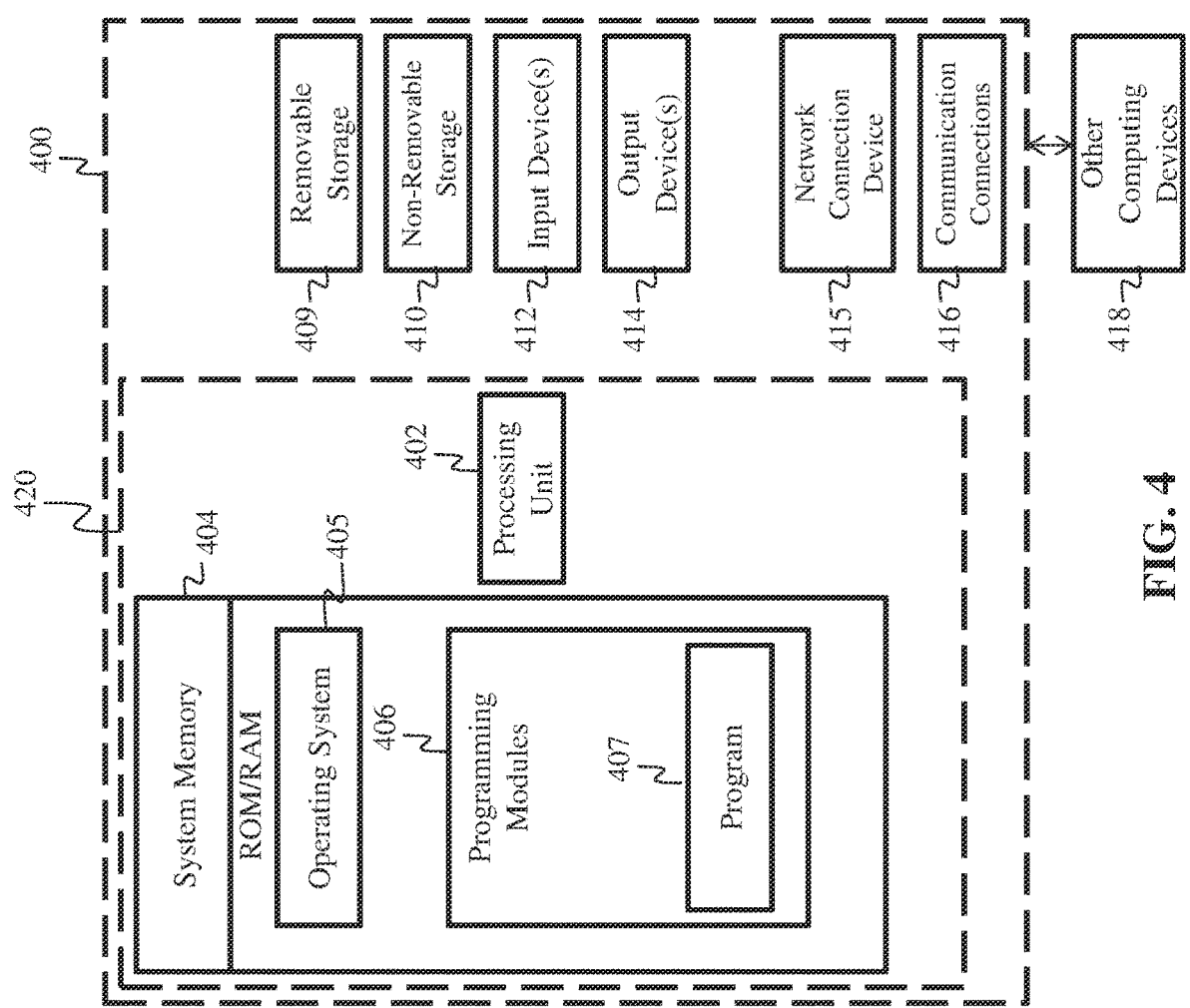
FIG. 4 is a block diagram depicting a system including an example computing system and other computing devices.

FIG. 4 is a block diagram of a system including an example computing device 400 and other computing devices. Consistent with the embodiments described herein, the aforementioned actions performed by 121, 131, or 102 may be implemented in a computing device, such as the computing device 400 of FIG. 4. Any suitable combination of hardware, software, or firmware may be used to implement the computing device 400. The aforementioned system, device, and processors are examples and other systems, devices, and processors may comprise the aforementioned computing device. Furthermore, computing device 400 may comprise an operating environment for system 100 and process 300, as described above. Process 300 may operate in other environments and are not limited to computing device 400.

With reference to FIG. 4, a system consistent with an embodiment may include a plurality of computing devices, such as computing device 400. In a basic configuration, computing device 400 may include at least one processing unit 402 and a system memory 404. Depending on the configuration and type of computing device, system memory 404 may comprise, but is not limited to, volatile (e.g. random-access memory (RAM)), non-volatile (e.g. read-only memory (ROM)), flash memory, or any combination or memory. System memory 404 may include operating system 405, and one or more programming modules 406. Operating system 405, for example, may be suitable for controlling computing device 400's operation. In one embodiment, programming modules 406 may include, for example, a program module 407 for executing the actions of 121, 131, 102. Furthermore, embodiments may be practiced in conjunction with a graphics library, other operating systems, or any other application program and is not limited to any particular application or system. This basic configuration is illustrated in FIG. 4 by those components within a dashed line 420.

Computing device 400 may have additional features or functionality. For example, computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computer storage media may include volatile and nonvolatile, removable and non-removable media implemented in any method or technology for storage of information, such as computer readable instructions, data structures, program modules, or other data. System memory 404, removable storage 409, and non-removable storage 410 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 400. Any such computer storage media may be part of device 400. Computing device 400 may also have input device(s) 412 such as a keyboard, a mouse, a pen, a sound input device, a camera, a touch input device, etc. Output device(s) 414 such as a display, speakers, a printer, etc. may also be included. Computing device 400 may also include a vibration device capable of initiating a vibration in the device on command, such as a mechanical vibrator or a vibrating alert motor. The aforementioned devices are only examples, and other devices may be added or substituted.

Computing device 400 may also contain a network connection device 415 that may allow device 400 to communicate with other computing devices 418, such as over a network in a distributed computing environment, for example, an intranet or the Internet. Device 415 may be a wired or wireless network interface controller, a network interface card, a network interface device, a network adapter or a LAN adapter. Device 415 allows for a communication connection 416 for communicating with other computing devices 418. Communication connection 416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 404, including operating system 405. While executing on processing unit 402, programming modules 406 (e.g. program module 407) may perform processes including, for example, one or more of the stages of the process 300 as described above. The aforementioned processes are examples, and processing unit 402 may perform other processes. Other programming modules that may be used in accordance with embodiments herein may include electronic mail and contacts applications, word processing applications, spreadsheet applications, database applications, slide presentation applications, drawing or computer-aided application programs, etc.

Generally, consistent with embodiments herein, program modules may include routines, programs, components, data structures, and other types of structures that may perform particular tasks or that may implement particular abstract data types. Moreover, embodiments herein may be practiced with other computer system configurations, including handheld devices, multiprocessor systems, microprocessor-based or programmable consumer electronics, minicomputers, mainframe computers, and the like. Embodiments herein may also be practiced in distributed computing environments where tasks are performed by remote processing devices that are linked through a communications network. In a distributed computing environment, program modules may be located in both local and remote memory storage devices.

Furthermore, embodiments herein may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments herein may also be practiced using other technologies capable of performing logical operations such as, for example, AND, OR, and NOT, including but not limited to mechanical, optical, fluidic, and quantum technologies. In addition, embodiments herein may be practiced within a general purpose computer or in any other circuits or systems.

Embodiments herein, for example, are described above with reference to block diagrams and/or operational illustrations of methods, systems, and computer program products according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments herein have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method implemented on a server for facilitating insurance policy application processing over a communications network, comprising the steps of:
   a) providing, over the communications network, a user interface configured for accepting input data from a customer from a particular state;
   b) accessing insurance agent records and identifying a set of insurance agents licensed in the particular state;
   c) broadcasting, over the communications network, a message to the set of insurance agents licensed in the particular state, the message indicating availability of the customer;
   d) receiving, over the communications network, an acceptance from a particular insurance agent licensed in the particular state;
   e) initiating a call, over the communications network, between the customer and the particular insurance agent;
   f) transmitting, over the communications network, a secure form to the particular insurance agent, wherein the form includes said input data and accepts further data entered into the form from the particular agent;
   g) creating a first data structure composed of an array of attribute-value pairs, wherein values of said attribute-value pairs include strings, said first data structure also including dependencies between attribute-value pairs, and hierarchical links between attribute-value pairs, encoding changes to the first data structure based on the input data and the further data, wherein said encoding includes: 1) for at least one attribute-value pair with a numerical value, generating a linked list that stores a first number of attribute-value pairs with a dependency on said attribute-value pair with a numerical value, wherein said first number is equal to said numerical value; 2) for each superior attribute-value with a hierarchical link to subordinate attribute-value pairs generating a second number of attribute-value pairs with a hierarchical link to said superior attribute-value pair, populating the first data structure based on the input data and the further data, and storing the first data structure in a first memory location;
   h) generating one or more ancillary documents based on the first data structure and transmitting to the customer, over the communications network, the one or more ancillary documents for electronic signature by, the customer;
   i) creating a second data structure composed of an array of attribute-value pairs, encoding changes to the second data structure based on a format of the second data structure, populating the second data structure by mapping data from the first data structure to the second data structure based on the format of the second data structure, wherein said mapping includes converting one or more values of attribute-value pairs in the first data structure, and storing the second data structure in a second memory location; and
   j) transmitting, via the communications network, the second data structure to a third party, wherein said transmitting initiates transmission of a health questionnaire to the customer.

2. The method of claim 1, wherein the step of providing, over the communications network, a user interface further comprises providing a graphical user interface on a web site.

3. The method of claim 2, wherein the step of broadcasting, over the communications network, a message further comprises broadcasting, over the communications network, a message to mobile computing devices of the set of insurance agents.

4. The method of claim 3, wherein the step of receiving, over the communications network, an acceptance further comprises receiving, over the communications network, a message from a mobile device of a particular insurance agent licensed in the particular state.

5. The method of claim 4, wherein the step of initiating a call, over the communications network, between the customer and the particular insurance agent further comprises initiating a call, over the public switched telephone network between the customer and the particular insurance agent.

6. The method of claim 5, wherein the step of generating one or more ancillary documents further comprises generating at least a legal agreement for the customer to sign with an electronic signature.

7. The method of claim 6, further comprising the step of:
transmitting, over the communications network, one or more ancillary documents to the customer for electronic signature.

8. The method of claim 7, further comprising the step of:
responsive to receiving an electronic signature by the customer on the one or more ancillary documents, transmitting a payment request to the customer.

9. The method of claim 8, wherein the step of storing the first data structure in a first memory location further comprises encrypting the first data structure before it is stored in the first memory location, and wherein the step of storing the second data structure in a second memory location further comprises encrypting the second data structure before it is stored in the second memory location.

10. A non-transitory computer-readable medium with instructions stored thereon, that when executed by a processor, perform the steps comprising:
a) providing, over a communications network, a user interface configured for accepting input data from a customer;
b) transmitting, over the communications network, a secure form to an insurance agent, wherein the form includes said input data and accepts further data entered into the form from the insurance agent;
c) creating a first data structure composed of an array of attribute-value pairs, wherein values of said attribute-value pairs include strings, said first data structure also including dependencies between attribute-value pairs, and hierarchical links between attribute-value pairs, encoding changes to the first data structure based on the input data and the further data, wherein said ding includes: 1) for at least one attribute-value pair with a numerical value, generating a linked list that stores a first number of attribute-value pairs with a dependency on said attribute-value pair with a numerical value, wherein said number is equal to said numerical value; 2) for each superior attribute-value pair with a hierarchical link to subordinate attribute-value pairs, generating a second number of attribute-value pairs with a hierarchical link to said superior attribute-value pair, populating the first data structure based on the input data and the further data, and storing the first data structure in a first memory location;
d) generating one or more ancillary documents based on the first data structure and transmitting to the customer, over the communications network, the one or more ancillary documents for electronic signature by the customer;
e) creating a second data structure composed of an array of attribute-value pairs, encoding changes to the second data structure based on a format of the second data structure, populating the second data structure by mapping data from the first data structure to the second data structure based on the format of the second data structure, wherein said mapping includes converting one or more values of attribute-value pairs in the first data structure, and storing the second data structure in a second memory location; and
f) transmitting, via the communications network, the second data structure to a third party, wherein said transmitting initiates transmission of a health questionnaire to the customer.

11. The non-transitory computer-readable medium of claim 10, wherein the step of providing, over the communications network, a user interface further comprises providing a graphical user interface on a web site.

12. The non-transitory computer-readable medium of claim 11, wherein the step of generating one or more ancillary documents further comprises generating at least a legal agreement for the customer to sign with an electronic signature.

13. The non-transitory computer-readable medium of claim 12, further comprising the step of:
transmitting, over the communications network, one or more ancillary documents to the customer for electronic signature.

14. The non-transitory computer-readable medium of claim 13, further comprising the step of:
responsive to receiving an electronic signature by the customer on the one or more ancillary documents, transmitting a payment request to the customer.

15. The non-transitory computer-readable medium of claim 14, wherein the step of storing the first data structure in a first memory location further comprises encrypting the first data structure before it is stored in the first memory location, and wherein the step of storing the second data structure in a second memory location further comprises encrypting the second data structure before it is stored in the second memory location.

16. A system for facilitating insurance policy application processing over a communications network, comprising:
a processor configured for:
a) providing, over a communications network, a user interface configured for accepting input data from a customer;
b) transmitting, over the communications network, a secure form to an insurance agent, wherein the form includes said input data and accepts further data entered into the form from the insurance agent;
c) creating a first data structure composed of an array of attribute-value pairs, wherein values of said attribute-value pairs include strings, said first data structure also including dependencies between attribute-value pairs, and hierarchical links between attribute-value pairs, encoding changes to the first data structure based on the input data and the further data, wherein said encoding includes: 1) for at least one attribute-value pair with a numerical value, generating a linked list that stores a first number of attribute-value pairs with a dependency on said attribute-value pair with a numerical value, wherein said first number is equal to said numerical value; 2) for each superior attribute-value pair with a hierarchical link to subordinate attribute-value pairs, generating a second number of attribute-value pairs with a hierarchical link to said superior attribute-value pair, and populating the first data structure based on the input data and the further data;

d) generating one or more ancillary documents based on the first data structure and transmitting to the customer, over the communications network, the one or more ancillary documents for electronic signature by the customer;

e) creating a second data structure composed of an array of attribute-value pairs, encoding changes to the second data structure based on a format of the second data structure, and populating the second data structure by mapping data from the first data structure to the second data structure based on the format of the second data structure, wherein said mapping includes converting one or more values of attribute-value pairs in the first data structure; and f) transmitting, via the communications network, the second data structure to a third party, wherein said transmitting initiates transmission of a health questionnaire to the customer;

a first memory for storing the first data structure; and a second memory for storing the second data structure.

17. The system of claim 16, wherein the step of providing, over the communications network, a user interface further comprises providing a graphical user interface on a web site.

18. The system of claim 17, wherein the step of generating one or more ancillary documents further comprises generating at least a legal agreement for the customer to sign with an electronic signature.

19. The system of claim 18, the processor further configured for:

transmitting, over the communications network, one or more ancillary documents to the customer for electronic signature.

20. The system of claim 19, wherein the processor encrypts the first data structure before it is stored in the first memory location, and wherein processor encrypts the second data structure before it is stored in the second memory location.

* * * * *